United States Patent
Matsumura et al.

(10) Patent No.: US 11,850,471 B2
(45) Date of Patent: Dec. 26, 2023

(54) MOTION PERFORMANCE ESTIMATE APPARATUS, MOTION PERFORMANCE ESTIMATE METHOD, AND PROGRAM

(71) Applicant: NIPPON TELEGRAPH AND TELEPHONE CORPORATION, Tokyo (JP)

(72) Inventors: Seiji Matsumura, Musashino (JP); Ken Watanabe, Musashino (JP); Toshitaka Kimura, Musashino (JP); Makio Kashino, Musashino (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 625 days.

(21) Appl. No.: 17/049,342

(22) PCT Filed: Apr. 3, 2019

(86) PCT No.: PCT/JP2019/014782
§ 371 (c)(1),
(2) Date: Oct. 21, 2020

(87) PCT Pub. No.: WO2019/208134
PCT Pub. Date: Oct. 31, 2019

(65) Prior Publication Data
US 2021/0052942 A1 Feb. 25, 2021

(30) Foreign Application Priority Data
Apr. 23, 2018 (JP) ................................ 2018-082077

(51) Int. Cl.
*A61B 5/22* (2006.01)
*A63B 24/00* (2006.01)
(Continued)

(52) U.S. Cl.
CPC .......... *A63B 24/0062* (2013.01); *A61B 5/165* (2013.01); *A61B 5/7275* (2013.01);
(Continued)

(58) Field of Classification Search
None
See application file for complete search history.

(56) References Cited

U.S. PATENT DOCUMENTS

| 10,921,886 B2* | 2/2021 | Connor | A61B 5/296 |
| 2008/0269644 A1* | 10/2008 | Ray | A61B 5/224 |
| | | | 600/587 |
| 2012/0316453 A1* | 12/2012 | Marcarian | G09B 19/003 |
| | | | 600/546 |

OTHER PUBLICATIONS

Shibahara et al., "Development of peak performance evaluation sheet and verification of the usefulness", Nippon Sport Science University Journal, vol. 46, Issue 1, Sep. 2016, pp. 67-70. (9 Pages with English Translation).

(Continued)

*Primary Examiner* — Sunit Pandya
(74) *Attorney, Agent, or Firm* — XSENSUS LLP

(57) ABSTRACT

An athletic activity performance estimation device estimates an athletic activity performance index relating to an athletic activity in which a subject performs a short-time action after a predetermined waiting time using information correlated with the state of tension of the subject as tension state information, an index indicating the subject's tension level as a tension state index, and an index indicating the quality of performance of an athletic activity of the subject as the athletic activity performance index. The athletic activity performance estimation device includes a tension state information acquirer that acquires the tension state information of the subject before starting the athletic activity, a tension state index calculator that calculates the tension state index of the (Continued)

subject from the tension state information, and an athletic activity performance index estimator.

12 Claims, 12 Drawing Sheets

(51) Int. Cl.
*A61B 5/00* (2006.01)
*A61B 5/16* (2006.01)

(52) U.S. Cl.
CPC ...... *A63B 24/0006* (2013.01); *A61B 2503/10* (2013.01); *A63B 2024/0012* (2013.01); *A63B 2024/0068* (2013.01)

(56) References Cited

OTHER PUBLICATIONS

Merati et al., "Autonomic modulations of heart rate variability and performances in short-distance elite swimmers", European Journal of Applied Physiology, vol. 115, Issue 4, Apr. 2015, pp. 825-835.
Hashimoto et al., "Examination of an analytical framework for predicting competitive performance", Health Science, Feb. 10, 2000, pp. 121-128 (22 Pages with English Translation).

\* cited by examiner

MOTION PERFORMANCE ESTIMATE APPARATUS, MOTION PERFORMANCE ESTIMATE METHOD, AND PROGRAM

CROSS-REFERENCE TO RELATED APPLICATIONS

The present application is based on PCT filing PCT/JP2019/014782, filed Apr. 3, 2019, which claims priority to JP 2018-082077, filed Apr. 23, 2018, the entire contents of each are incorporated herein by reference.

TECHNICAL FIELD

The present invention relates to a technique for estimating the performance of an athletic activity of a subject.

BACKGROUND ART

NPL 1 compares the best time in a competition (of 50 m freestyle or 100 m freestyle) in a certain swimming competition season (September to December) with the autonomic nervous activity of a certain day (not on the day of competition) during the season and reports the following relationship as a result of the comparison.

(1) There was a positive correlation between the magnitude of parasympathetic (vagal) nerve activity upon waking and the 50 m season best time. That is, an athlete having more parasympathetic activity exhibits a slower time and lower performance. However, no correlation was found with the 100 m season best time.

(2) A higher value of sympathetic activity/parasympathetic activity (meaningfully similar to sympathetic activity in most cases) immediately after training is associated with a faster 100 m season best time, that is, higher performance. However, no correlation was found with the 50 m season best time.

CITATION LIST

Non Patent Literature

[NPL 1] Giampiero Merati, Martina Anna Maggioni, Pietro Luigi Invernizzi, Claudio Ciapparelli, Luca Agnello, Arsenio Veicsteinas, and Paolo Castiglioni, "Autonomic modulations of heart rate variability and performances in short-distance elite swimmers", European Journal of Applied Physiology, Volume 115, Issue 4, pp. 825-835, April 2015.

SUMMARY OF THE INVENTION

Technical Problem

NPL 1 notes the correlation between a measurement result of a physiological state of one day during a competition season, which is not the day of competition, and a condition (best time) of the competition season, and does not evaluate the relation between a physiological state before a competition and performance in the competition and thus does not reveal whether or not there is a correlation between parasympathetic activity before a competition and performance in the competition. Thus, with NPL 1, it is not possible to predict the performance of an athletic activity that a subject is going to perform on the basis of the subject's state before the competition.

Therefore, it is an object of the present invention to provide a technique for estimating the performance of an athletic activity that a subject is going to perform on the basis of the subject's state before starting the athletic activity.

Means for Solving the Problem

An aspect of the present invention provides an athletic activity performance estimation device for estimating an athletic activity performance index relating to an athletic activity in which a subject performs a short-time action after a predetermined waiting time using information correlated with a state of tension of the subject as tension state information, an index indicating a tension level of the subject as a tension state index, and an index indicating a quality of performance of an athletic activity of the subject as the athletic activity performance index, the athletic activity performance estimation device including: a tension state information acquirer configured to acquire the tension state information of the subject before starting the athletic activity; a tension state index calculator configured to calculate the tension state index of the subject from the tension state information; and an athletic activity performance index estimator configured to estimate the athletic activity performance index of the subject from the tension state index on the basis of a pre-given correlation between the tension state index and the athletic activity performance index.

An aspect of the present invention provides an athletic activity performance estimation device for estimating an athletic activity performance index relating to an athletic activity in which a subject performs a short-time action after a predetermined waiting time using information correlated with a state of tension of the subject as tension state information, and an index indicating a quality of performance of an athletic activity of the subject as the athletic activity performance index, the athletic activity performance estimation device including: a tension state information acquirer configured to acquire the tension state information of the subject before starting the athletic activity; and an athletic activity performance index estimator configured to estimate the athletic activity performance index of the subject from the tension state information on the basis of a pre-given correlation between the tension state information and the athletic activity performance index.

Effects of the Invention

According to the present invention, it is possible to estimate the performance of an athletic activity that a subject is going to perform on the basis of the subject's state before starting the athletic activity.

DESCRIPTION OF EMBODIMENTS

Figure 1:
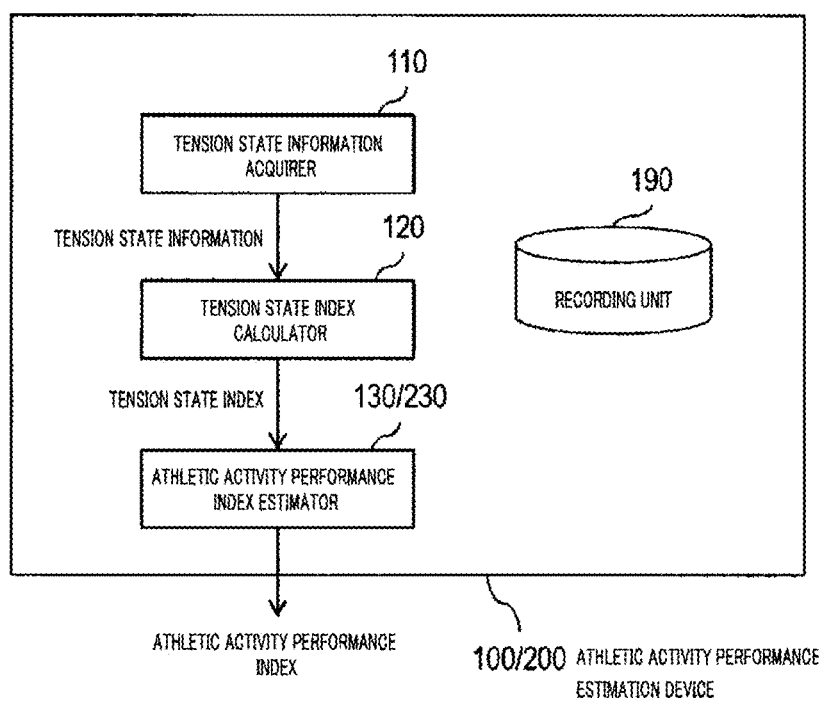
FIG. 1 is a block diagram showing an example of a configuration of an athletic activity performance estimation device 100/200.

Hereinafter, embodiments of the present invention will be described in detail. Components having the same functions are given the same reference signs and redundant description is omitted.

Technical Background

Athletic activities of interest in the invention of each embodiment are those in which performance tends to be affected by the subject's state before the competition, namely, those of so-called single-impact sports in which the subject performs a short action after a predetermined waiting time and the single action determines the winner. Examples include long jump, high jump, ski/snowboard jump (for example, one-make and big air), swimming dive, and soccer penalty kick.

It is conceivable that, in such a single-impact athletic activity, the subject can adjust the timing of starting an action by himself or herself and the quality of the performance tends to be affected by how that timing is taken and how much force is applied at that time.

Attention is paid particularly to a state of tension as a state of the subject. This is because it is conceivable that appropriate tension can improve performance, while insufficient or excessive tension may prevent intended performance from being achieved. With an appropriate state of tension, how to determine the timing of starting an athletic activity is less likely to vary, and as a result, the probability of being able to take off with an ideal force at an ideal timing of takeoff is expected to be high, for example, in a jump competition. On the other hand, with an insufficient or excessive state of tension, how to determine the timing of starting an athletic activity or how to apply force is likely to vary, and as a result, the timing of takeoff deviates, force fails to be applied, or too much force is applied, and therefore it can be considered difficult to achieve good performance.

If a subject can determine whether or not he or she is in a state of being able to perform an athletic activity with good performance, and if not, whether it is because of insufficient tension or excessive tension, and the like by knowing his or her current state of tension, the subject is also expected to be able to control himself or herself to enter a state in which he or she is able to achieve better performance. In particular, it is preferable for the performance that the subject is going to perform in a competition to be able to be estimated based on a state of tension before the competition which is considered to tend to affect the performance in the competition.

Thus, the invention of each embodiment provides a technique for estimating the quality of the performance of an athletic activity that a subject is going to perform on the basis of information correlated with a state of tension obtained by measuring the subject. Here, the information correlated with the state of tension includes, for example, information on a physiological state of the subject such as a heartbeat, a pulse wave, sweating, or eye movement, a facial expression of the subject, a body movement (behavior) of the subject, and a voice of the subject (for example, the pitch of the voice). The reason why these can be information correlated with the state of tension is as follows. It is known that, in a state of tension, a physiological state change such as an increase in heart rate or mental sweating is observed due to activation of sympathetic nervous activity which is one of the autonomic nervous activities. Therefore, it is possible to measure the state of tension by measuring the physiological state. In addition, changes such as hardening of a facial expression, expression of a specific body movement, and rising of the voice are also observed in tension. Therefore, the state of tension can also be measured by measuring these changes.

First Embodiment

An athletic activity performance estimation device 100 estimates an athletic activity performance index relating to an athletic activity in which a subject performs a short-time action after a predetermined waiting time. Here, the athletic activity performance index is an index indicating the quality (level) of the performance of the athletic activity of the subject.

Figure 2:
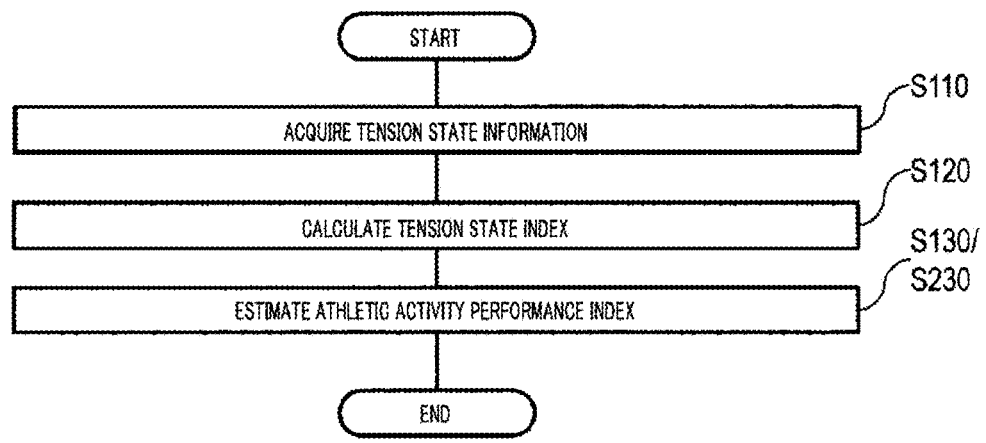
FIG. 2 is a flowchart showing an example of an operation of the athletic activity performance estimation device 100/200.

Hereinafter, the athletic activity performance estimation device 100 will be described with reference to FIGS. 1 and 2. FIG. 1 is a block diagram showing a configuration of the athletic activity performance estimation device 100. FIG. 2 is a flowchart showing an operation of the athletic activity performance estimation device 100. As shown in FIG. 1, the athletic activity performance estimation device 100 includes a tension state information acquirer 110, a tension state index calculator 120, an athletic activity performance index estimator 130, and a recording unit 190. The recording unit 190 is a component that appropriately records information necessary for the processing of the athletic activity performance estimation device 100.

The operation of the athletic activity performance estimation device 100 will be described with reference to FIG. 2.

[Tension State Information Acquirer 110]

In S110, the tension state information acquirer 110 acquires and outputs tension state information that is information correlated with the state of tension of the subject by measuring the subject before starting an athletic activity. Examples of the tension state information include, for example, biological information correlated with autonomic nervous activity of the subject, a facial expression of the subject, a body movement of the subject, and a voice of the subject. Examples of the biological information correlated with the autonomic nervous activity include, for example, a heart rate, skin electrical activity (the amount of sweating), eye movement, and a fingertip pulse wave. If it is assumed that the athletic activity performance estimation device 100 is used before the competition, it is preferable for measurement to be able to be performed non-invasively with a simple device and for a measurement result to be able to be obtained in a short time (for example, about five minutes) before an athletic activity starts.

The purpose of the tension state information acquirer 110 is to acquire, from the subject, information correlated with the state of tension of the subject (tension state information) which is used when the tension state index calculator 120 that will be described later calculates an index indicating the level of the tension of the subject (a tension state index). Thus, the tension state information to be acquired may be any information as long as the index indicating the level of the tension of the subject can be calculated therefrom. In other words, the tension state information acquirer 110 may measure and acquire, as tension state information, not only the biological information, body movement, voice, and the like of the subject described above but also other features that the subject exhibits along with the tension state.

[Tension State Index Calculator 120]

In S120, the tension state index calculator 120 calculates and outputs a tension state index, which is an index indicating the level of the tension of the subject, from the tension state information acquired in S110. The tension state index may be any index as long as the level (degree) of the tension of the subject can be identified therefrom.

Hereinafter, the case where electrocardiographic data (an electrocardiogram) acquired using an electrocardiograph is used as tension state information and an index which can estimate the magnitude of autonomic nervous activity (an autonomic nerve activity index) is used as an index indicating the level of tension (a tension state index) will be described as an example. In this case, the tension state index calculator 120 performs a heart rate variability analysis (Heart Rate Variability: HRV) on the electrocardiographic data acquired in S110 to obtain an HF component (High Frequency component) and an LF component (Low Frequency component) during a measurement period and calculates an autonomic nervous activity index that is a series of values of the LF component/HF component which is the ratio between the two components. Here, the LF component/HF component is an index indicating that the sympathetic nervous activity is active, and a higher value of this index indicates higher tension (a higher degree of tension).

The tension state index can also be calculated assuming that the tension state index is a value of a predetermined monotonically increasing function regarding the LF component/HF component. When a function is referred to as a monotonically increasing function, it is assumed that the function may be a narrowly monotonically increasing function or a broadly monotonically increasing function.

As described above, if a tension state index correlated with tension state information is known, the tension state index can be calculated from the tension state information on the basis of the relation.

[Athletic Activity Performance Index Estimator 130]

In S130, the athletic activity performance index estimator 130 estimates and outputs an athletic activity performance index that is an index indicating the quality of the performance of the athletic activity of the subject from the tension state index calculated in S120 on the basis of a pre-given correlation between the tension state index and the athletic activity performance index.

Here, the athletic activity performance index is a measure for identifying the quality of the performance and examples thereof include a score indicating a result of the athletic activity and the timing or strength of a movement in the athletic activity which affects the score. Examples of the timing or strength of a movement in the athletic activity which affects the score include the height of a jump in a jump competition, the strength of force of the foot at takeoff, the angle at takeoff, and the timing of takeoff (the deviation of (a predicted value of) the actual takeoff time from an ideal takeoff time).

Figure 3:
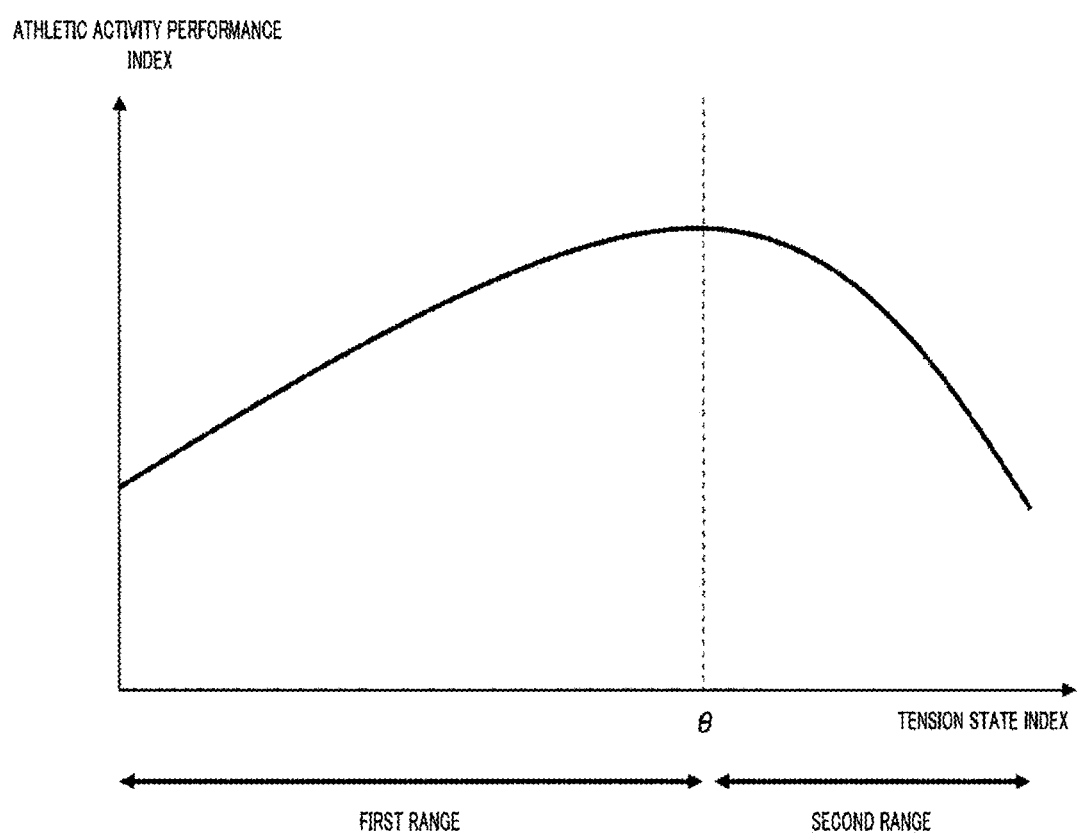

The correlation between the tension state index and the athletic activity performance index is such that the level of the performance monotonically increases as the tension increases in a range in which the tension state index is smaller than a predetermined threshold θ (a first range) and monotonically decreases as the tension increases in a range in which the tension state index is greater than the predetermined threshold θ (a second range) as shown in FIG. 3. Here, the monotone increase includes a broad monotone increase and a narrow monotone increase and the broad monotone increase (narrow monotone increase) of the level of the performance as the tension increases indicates that $y_1 \leq y_2$ ($y_1 < y_2$) is satisfied when $x_1 < x_2$ where $y_1$ is the level of the performance when the degree of tension is $x_1$ and $y_2$ is the level of the performance when the degree of tension is $x_2$. Similarly, the monotone decrease includes a broad monotone decrease and a narrow monotone decrease and the broad monotone decrease (narrow monotone decrease) of the level of the performance as the tension increases indicates that $y_1 \geq y_2$ ($y_2 > y_2$) is satisfied when $x_1 < x_2$.

In summary, the correlation between the tension state index and the athletic activity performance index is such that the athletic activity performance index monotonically increases with respect to the tension state index in a range in which the tension state index is smaller than a predetermined threshold θ and monotonically decreases with respect to the tension state index in a range in which the tension state index is greater than the threshold θ.

A function whose input is a tension state index and output is an athletic activity performance index and which has the properties as shown in FIG. 3 (that is, monotonically increasing in a range up to a predetermined threshold θ and monotonically decreasing in a range exceeding the threshold θ) will hereinafter be referred to as a performance function.

The performance function is obtained in advance. For example, data of a tension state index calculated from tension state information acquired before an athletic activity starts and an athletic activity performance index relating to an athletic activity actually performed thereafter may be analyzed for one or more subjects and the distribution of the data may then be matched with a function having the above properties to determine parameters of the function, thus obtaining a performance function. In another method, a performance function may be obtained, for example, by training function parameters through a machine learning method using data of the tension state index and the athletic activity performance index as training data.

When the correlation between the tension state index and the athletic activity performance index is given as a performance function, the athletic activity performance index estimator 130 estimates the athletic activity performance index from the tension state index calculated in S120 using the performance function.

Figure 4:
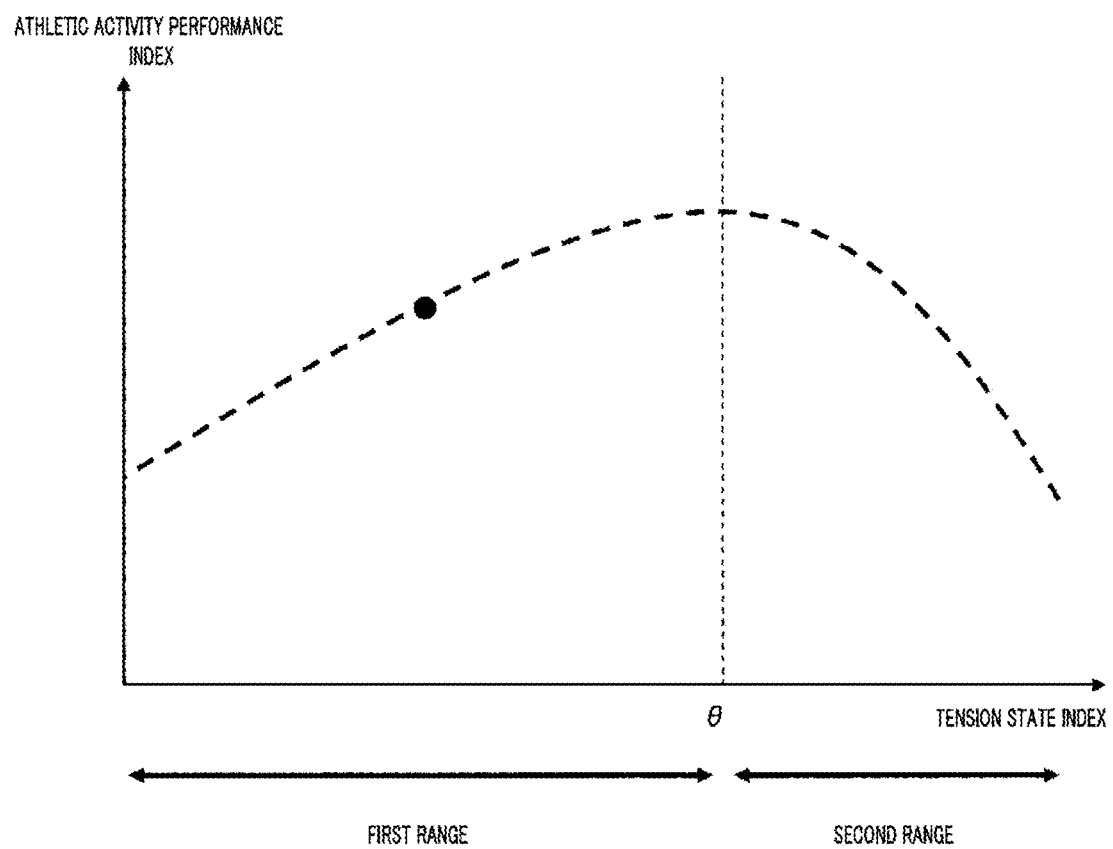
FIG. 4 is a diagram showing an example of an output of the athletic activity performance estimation device 100.

The athletic activity performance index estimator 130 may output only the estimated athletic activity performance index or may visually output the athletic activity performance index as information in a form in which the position of the estimated athletic activity performance index on a curve of the performance function can be identified as shown in FIG. 4.

When a plurality of measures (for example, a set of the strength of force of the foot at takeoff and the timing of takeoff) are used, a combination of measures may be set as an athletic activity performance index or, for example, a weighted sum of the measures may be set as the athletic activity performance index.

(Modification 1)

The athletic activity performance estimation device 100 may estimate the athletic activity performance index using a plurality of performance functions (hereinafter referred to as reference performance functions). In this case, for example, a correction unit (not shown) of the athletic activity performance estimation device 100 generates, in accordance with a subject who is subjected to estimation of the athletic activity performance index, a performance function for the subject used in the athletic activity performance index estimator 130 using the reference performance functions before executing the processing of S110 to S130.

(Modification 2)

Instead of giving the correlation between the tension state index and the athletic activity performance index as a performance function, an athletic activity performance estimation model whose input is the tension state index and output is the athletic activity performance index may be trained through machine learning and the athletic activity performance index estimator 130 may be configured to estimate an athletic activity performance index using the trained athletic activity performance estimation model.

In this case, parameters of the athletic activity performance estimation model are trained through a machine learning method using a set of a tension state index calculated from tension state information acquired before an athletic activity starts and an athletic activity performance index of an athletic activity actually performed thereafter for one or more subjects as training data. Specifically, the training is performed by repeating a process of updating the parameters of the athletic activity performance estimation model such that an athletic activity performance index obtained from a tension state index in the training data using the athletic activity performance estimation model approaches an athletic activity performance index corresponding to the tension state index (that is, correct answer data). The training starts after giving appropriate initial values to the parameters of the athletic activity performance estimation model.

According to the invention of the present embodiment, it is possible to estimate the performance of an athletic activity that a subject is going to perform on the basis of the subject's state before starting the athletic activity.

Second Embodiment

An athletic activity performance estimation device 200 estimates an athletic activity performance index relating to an athletic activity in which a subject performs a short-time action after a predetermined waiting time.

Hereinafter, the athletic activity performance estimation device 200 will be described with reference to FIGS. 1 and 2. FIG. 1 is a block diagram showing a configuration of the athletic activity performance estimation device 200. FIG. 2 is a flowchart showing an operation of the athletic activity performance estimation device 200. As shown in FIG. 1, the athletic activity performance estimation device 200 includes a tension state information acquirer 110, a tension state index calculator 120, an athletic activity performance index estimator 230, and a recording unit 190. The recording unit 190 is a component that appropriately records information necessary for the processing of the athletic activity performance estimation device 200. That is, the athletic activity performance estimation device 200 differs from the athletic activity performance estimation device 100 in that the athletic activity performance estimation device 200 includes the athletic activity performance index estimator 230 instead of the athletic activity performance index estimator 130.

The operation of the athletic activity performance estimation device 200 will be described with reference to FIG. 2. Hereinafter, the athletic activity performance index estimator 230 will be described.

[Athletic Activity Performance Index Estimator 230]

In S230, the athletic activity performance index estimator 230 estimates and outputs an athletic activity performance index that is an index indicating the quality of the performance of the athletic activity of the subject from the tension state index calculated in S120 on the basis of a pre-given correlation between the tension state index and the athletic activity performance index.

Figure 5:
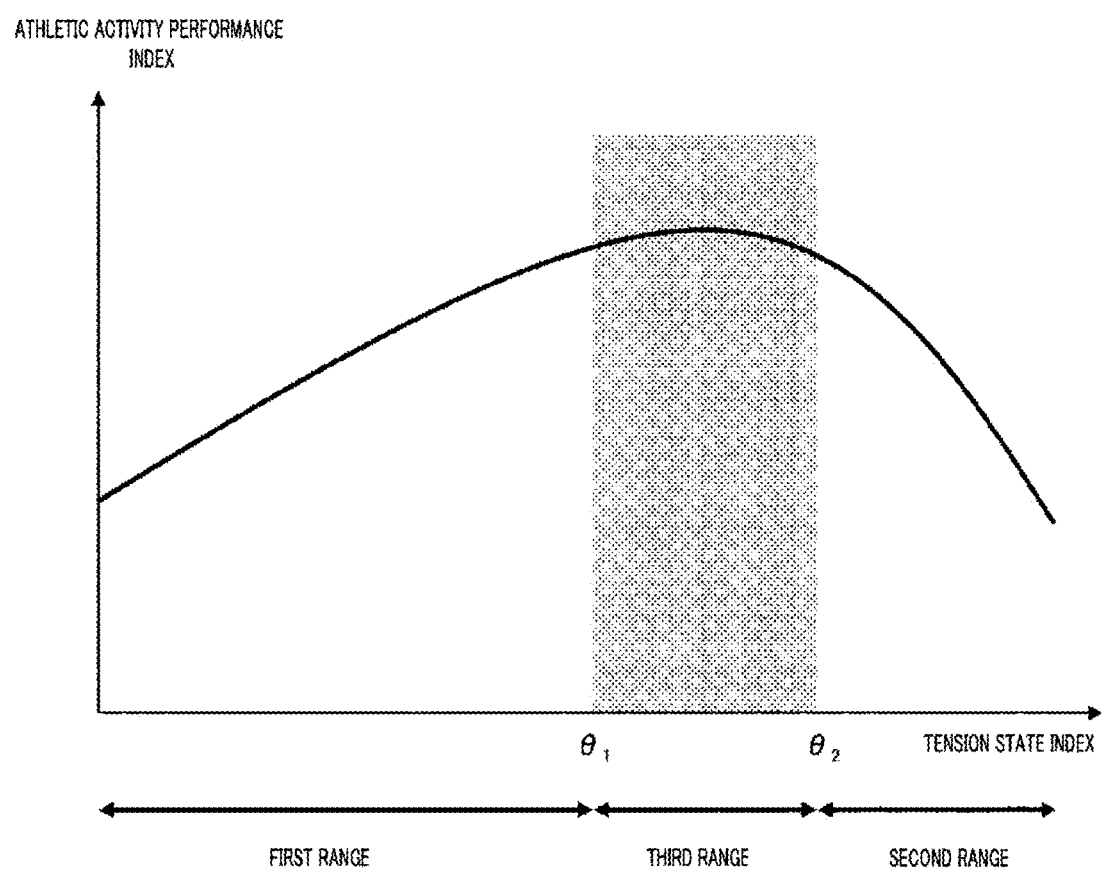
FIG. 5 is a diagram showing an example of a relationship between a tension state index and an athletic activity performance index.

Appropriate tension leads to high performance as described in <Technical background>. Thus, a range of the tension state index where good performance can be achieved is defined as a third range, a range in which the degree of tension is less than the third range is defined as a first range, and a range in which the degree of tension is higher than the third range is defined as a second range as shown in FIG. 5, and it is estimated to which range the tension state index belongs. This is considered to make it possible to easily identify whether the subject is in a tension state in which good performance can be achieved, in an insufficient tension state, or in an excessive tension state.

In other words, the athletic activity performance index estimator 230 estimates and outputs an athletic activity performance index in a form in which it is possible to identify whether the degree of tension (tension level) indicated by the tension state index corresponds to a state in which good performance can be achieved and whether the degree of tension corresponds to an insufficient tension state or an excessive tension state if it corresponds to a state in which good performance cannot be achieved.

For example, the athletic activity performance index estimator 230 sets a lower limit of the tension state index in the third range as a first threshold $\theta_1$ and an upper limit of the tension state index in the third range as a second threshold $\theta_2$ and compares the tension state index with the first threshold $\theta_1$ and the second threshold $\theta_2$ to estimate an athletic activity performance index as follows.

(1) When the tension state index is smaller than the first threshold $\theta_1$, information indicating that the tension is insufficient to achieve good performance is estimated as the athletic activity performance index.

(2) When the tension state index is greater than the first threshold $\theta_1$ and smaller than the second threshold $\theta_2$, information indicating that good performance can be achieved (an ideal performance can be achieved) is estimated as the athletic activity performance index.

(3) When the tension state index is greater than the second threshold $\theta_2$, information indicating that the tension is too much to achieve good performance is estimated as the athletic activity performance index.

When the tension state index is equal to the first threshold $\theta_1$, which is a boundary value, the athletic activity performance index may be estimated as information indicating that the tension is insufficient to achieve good performance or may be estimated as information indicating that good performance can be achieved. Similarly, when the tension state index is equal to the second threshold $\theta_2$, which is a boundary value, the athletic activity performance index may be estimated as information indicating that good performance can be achieved or may be estimated as information indicating that the tension is too much to achieve good performance.

The following is a summary of the above. $\theta_1$ and $\theta_2$ are assumed as thresholds satisfying $\theta_1<\theta_2$. Then, the athletic activity performance index estimator 230 estimates as an athletic activity performance index indicating that the tension is insufficient to achieve good performance if the tension state index is smaller than $\theta_1$. The athletic activity performance index estimator 230 estimates as an athletic activity performance index indicating that good performance can be achieved if the tension state index is greater than $\theta_1$ and smaller than $\theta_2$. The athletic activity performance index estimator 230 estimates as an athletic activity performance index indicating that the tension is too much to achieve good performance if the tension state index is greater than $\theta_2$.

Figure 6:
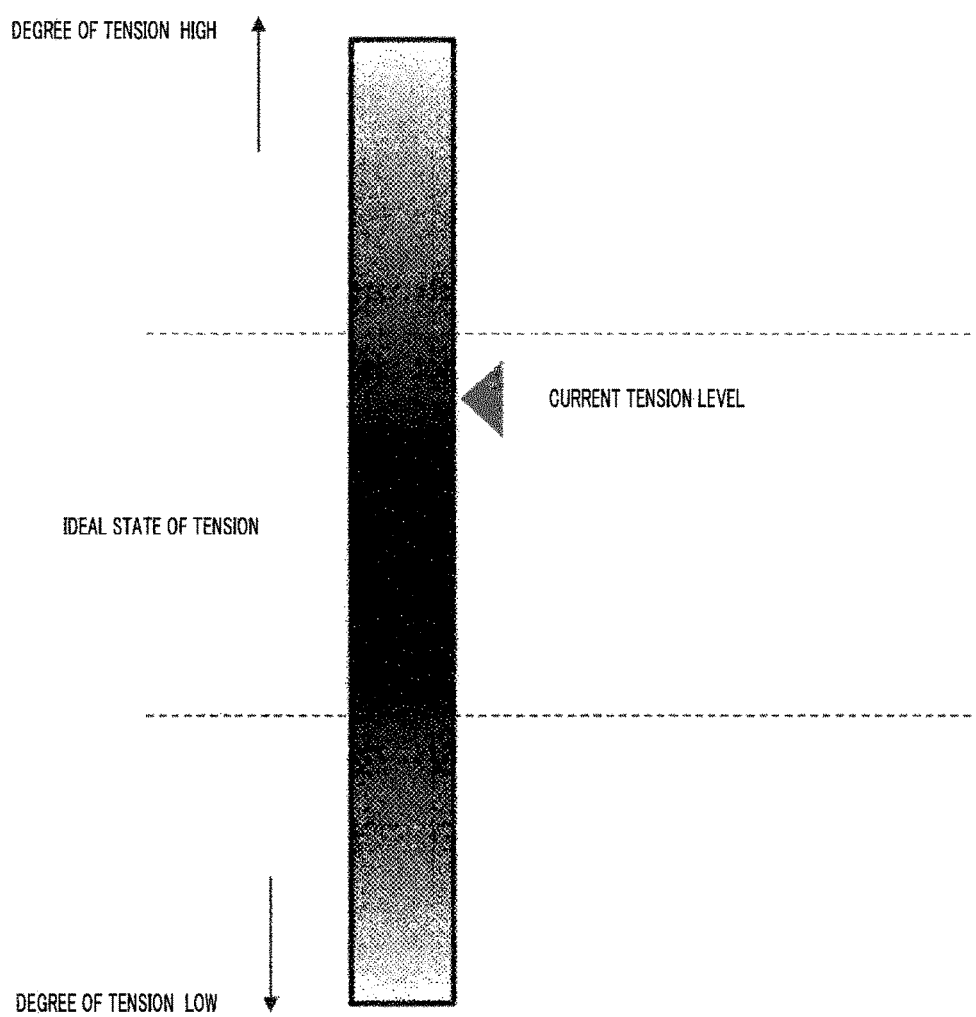
FIG. 6 is a diagram showing an example of an output of the athletic activity performance estimation device 200.

The athletic activity performance index estimator 230 may output only the estimated athletic activity performance index or may output the athletic activity performance index as information in a form in which whether or not the current tension level corresponds to an ideal tension state (a state in which good performance can be achieved) can be visually identified as shown in FIG. 6.

According to the invention of the present embodiment, it is possible to estimate the performance of an athletic activity that a subject is going to perform on the basis of the subject's state before starting the athletic activity.

Third Embodiment

In the first and second embodiments, an athletic activity performance index is estimated based on the correlation between a tension state index and the athletic activity performance index after calculating the tension state index from tension state information acquired from the subject. However, because a certain correlation is established between the tension state information and the athletic activity performance index, the athletic activity performance index can also be estimated based on the direct correlation between the tension state information and the athletic activity performance index. Thus, an embodiment in which an athletic activity performance index is estimated based on the correlation between tension state information and the athletic activity performance index will be described here.

An athletic activity performance estimation device 300 estimates an athletic activity performance index relating to an athletic activity in which a subject performs a short-time action after a predetermined waiting time.

Figure 7:
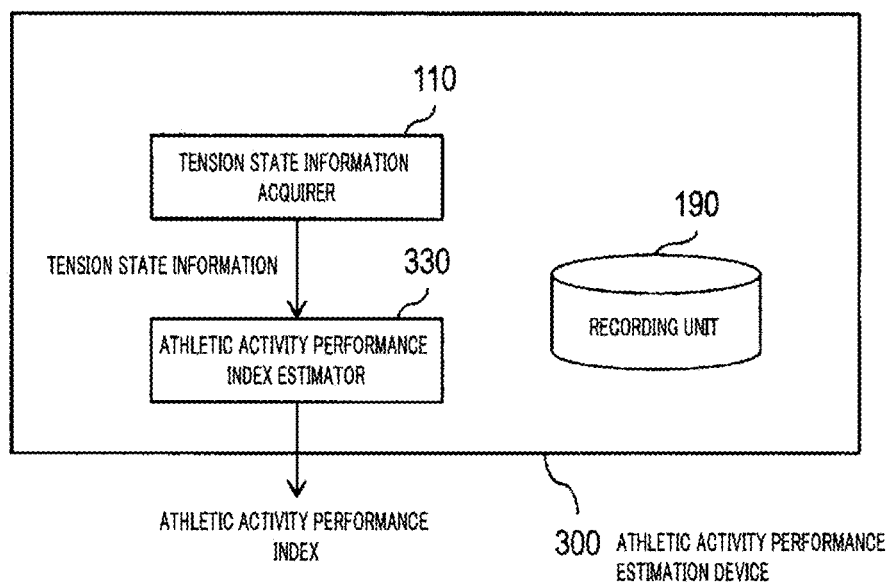
FIG. 7 is a block diagram showing an example of a configuration of an athletic activity performance estimation device 300.
Figure 8:
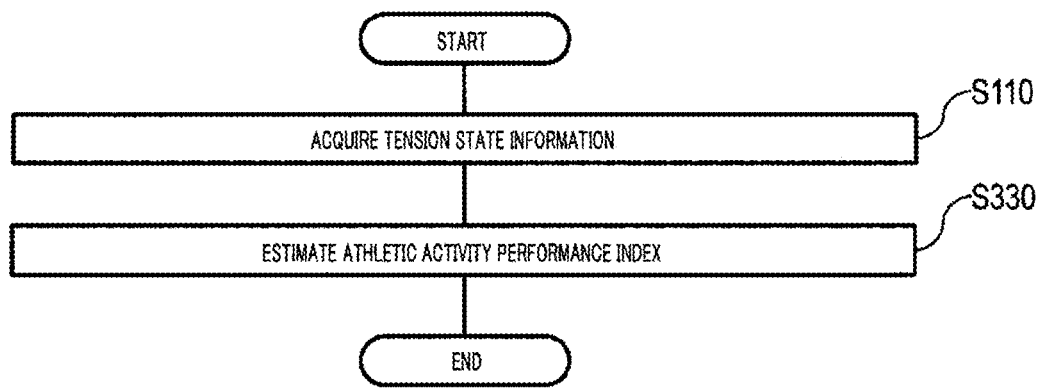
FIG. 8 is a flowchart showing an example of the operation of the athletic activity performance estimation device 300.

Hereinafter, the athletic activity performance estimation device 300 will be described with reference to FIGS. 7 and 8. FIG. 7 is a block diagram showing a configuration of the athletic activity performance estimation device 300. FIG. 8 is a flowchart showing an operation of the athletic activity performance estimation device 300. As shown in FIG. 7, the athletic activity performance estimation device 300 includes a tension state information acquirer 110, an athletic activity performance index estimator 330, and a recording unit 190. The recording unit 190 is a component that appropriately records information necessary for the processing of the athletic activity performance estimation device 300. That is, the athletic activity performance estimation device 300 differs from the athletic activity performance estimation device 100/200 in that the athletic activity performance estimation device 300 does not include the tension state index calculator 120. The athletic activity performance estimation device 300 also differs from the athletic activity performance estimation device 100/200 in that the athletic activity performance estimation device 300 includes the athletic activity performance index estimator 330 instead of the athletic activity performance index estimator 130/230.

The operation of the athletic activity performance estimation device 300 will be described with reference to FIG. 8. Hereinafter, the athletic activity performance index estimator 330 will be described.

[Athletic Activity Performance Index Estimator 330]

In S330, the athletic activity performance index estimator 330 estimates and outputs an athletic activity performance index that is an index indicating the quality of the performance of the athletic activity of the subject from tension state information acquired in S110 on the basis of a pre-given correlation between the tension state information and the athletic activity performance index.

Let us consider the correlation between the tension state information and the athletic activity performance index separately for cases (1) where there is a monotonically increasing relationship between the tension state information and the tension level and (2) where there is a monotonically decreasing relationship between the tension state information and the tension level.

Figure 9:
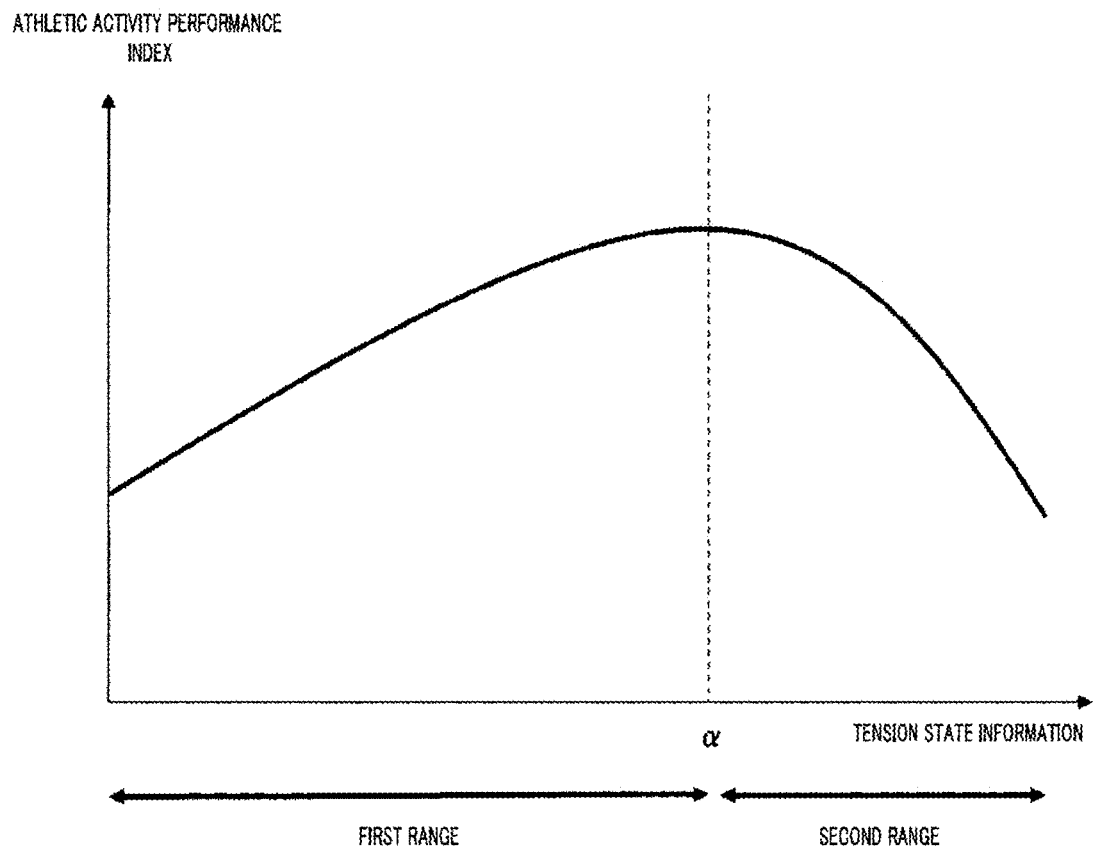
FIG. 9 is a diagram showing an example of a relationship between tension state information and an athletic activity performance index.

(1) A Case Where There is a Monotonically Increasing Relationship Between the Tension State Information and the Tension Level In this case, the correlation between the tension state information and the athletic activity performance index is as shown in FIG. 9. That is, the correlation between the tension state information and the athletic activity performance index is represented using a function having a predetermined threshold $\alpha$ such that the athletic activity performance index monotonically increases with respect to the tension state information in a range in which the tension state information is smaller than the predetermined threshold $\alpha$ (a first range) and monotonically decreases with respect to the tension state information in a range in which the tension state information is greater than the threshold $\alpha$ (a second range).

Figure 10:
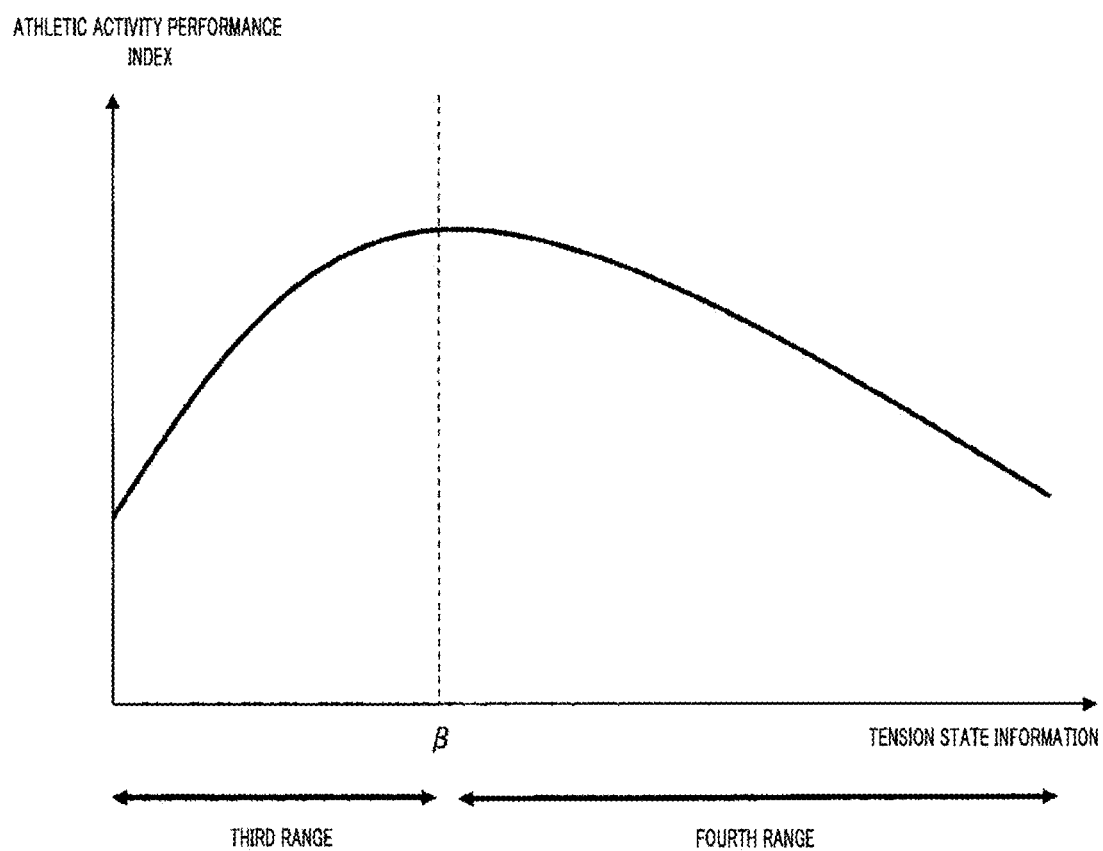
FIG. 10 is a diagram showing an example of a relationship between tension state information and an athletic activity performance index.

(2) A Case Where There is a Monotonically Decreasing Relationship Between the Tension State Information and the Tension Level In this case, the correlation between the tension state information and the athletic activity performance index is as shown in FIG. 10. That is, the correlation between the tension state information and the athletic activity performance index is represented using a function having a predetermined threshold $\beta$ such that the athletic activity performance index monotonically increases with respect to the tension state information in a range in which the tension state information is smaller than the predetermined threshold $\beta$ (a third range) and monotonically decreases with respect to the tension state information in a range in which the tension state information is greater than the threshold $\beta$ (a fourth range).

That is, in any case, the correlation between the tension state information and the athletic activity performance index is such that the athletic activity performance index monotonically increases with respect to the tension state information in a range in which the tension state information is smaller than a predetermined threshold and monotonically decreases with respect to the tension state information in a range in which the tension state information is greater than the threshold.

(Modification 1)

Instead of giving the correlation between the tension state information and the athletic activity performance index as a function as described above, an athletic activity performance estimation model whose input is the tension state information and output is the athletic activity performance index may be trained through machine learning and the athletic activity performance index estimator 330 may be configured to estimate an athletic activity performance index using the trained athletic activity performance estimation model.

In this case, parameters of the athletic activity performance estimation model are trained through a machine learning method using a set of tension state information acquired before an athletic activity starts and an athletic activity performance index of an athletic activity actually performed thereafter for one or more subjects as training data. Specifically, the training is performed by repeating a process of updating the parameters of the athletic activity performance estimation model such that an athletic activity performance index obtained from tension state information in the training data using the athletic activity performance estimation model approaches an athletic activity performance index corresponding to the tension state information (that is, correct answer data). The training starts after giving appropriate initial values to the parameters of the athletic activity performance estimation model.

(Modification 2)

The athletic activity performance index may be estimated using a range of the tension state information in which good performance can be achieved, similar to the second embodiment (see FIG. 5).

Figure 11:
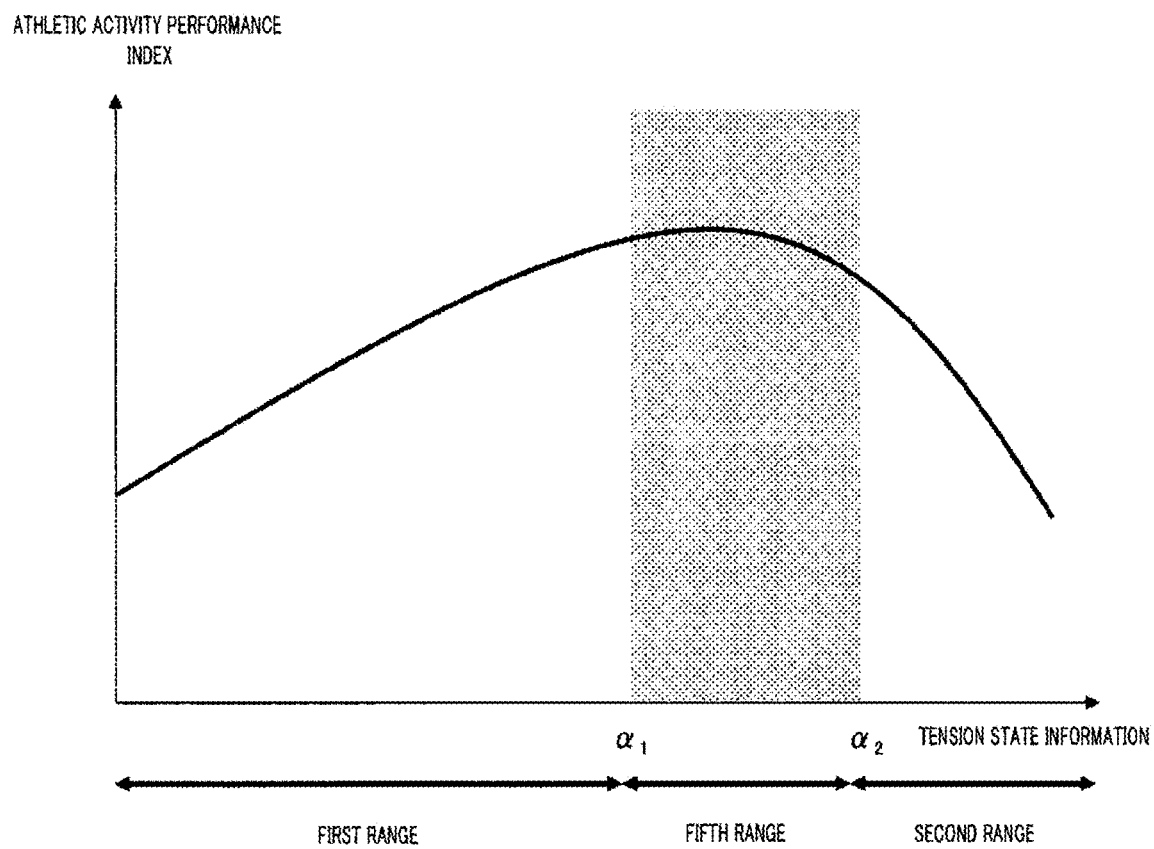
FIG. 11 is a diagram showing an example of a relationship between tension state information and an athletic activity performance index.
Figure 12:
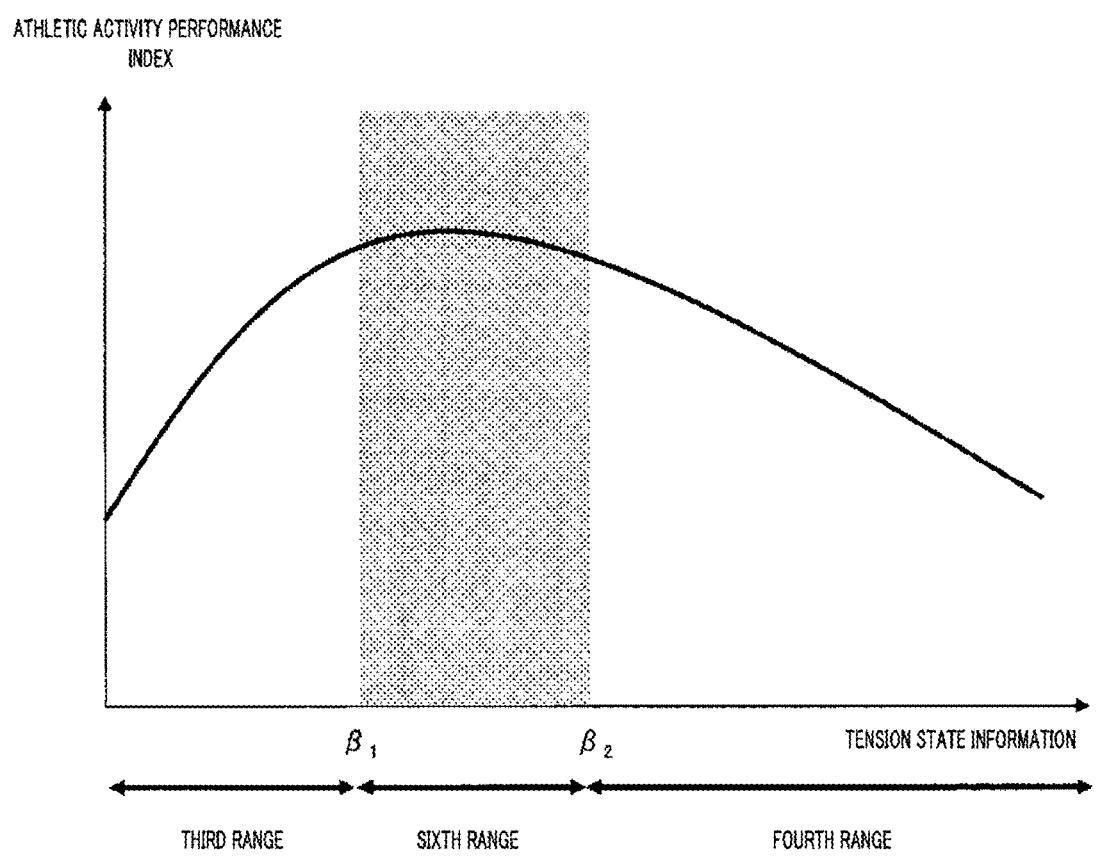
FIG. 12 is a diagram showing an example of a relationship between tension state information and an athletic activity performance index.

The athletic activity performance index can be considered in two different modes corresponding to the cases (1) where there is a monotonically increasing relationship between the tension state information and the tension level (see FIGS. 11) and (2) where there is a monotonically decreasing relationship between the tension state information and the tension level (see FIG. 12).

(1) A Case Where There is a Monotonically Increasing Relationship Between the Tension State Information and the Tension Level $\alpha_1$ and $\alpha_2$ are assumed as thresholds satisfying $\alpha_1 < \alpha_2$. The athletic activity performance index indicates that the tension is insufficient to achieve good performance if the tension state information is smaller than $\alpha_1$. The athletic activity performance index indicates that good performance can be achieved if the tension state information is greater than $\alpha_1$ and smaller than $\alpha_2$. The athletic activity performance index indicates that the tension is too much to achieve good performance if the tension state information is greater than $\alpha_2$.

(2) A Case Where There is a Monotonically Decreasing Relationship Between the Tension State Information and the Tension Level $\beta_1$ and $\beta_2$ are assumed as thresholds satisfying $\beta_1 < \beta_2$. The athletic activity performance index indicates that the tension is too much to achieve good performance if the tension state information is smaller than $\beta_1$, indicates that good performance can be achieved if the tension state information is greater than $\beta_1$ and smaller than $\beta_2$, and indicates that the tension is insufficient to achieve good performance if the tension state information is greater than $\beta_2$.

The following is a summary of the above. When there is a monotonically increasing relationship between the tension state information and the tension level with $\alpha_1$ and $\alpha_2$ being thresholds satisfying $\alpha_1 < \alpha_2$, the athletic activity performance index estimator 330 estimates an athletic activity performance index indicating that the tension is insufficient to achieve good performance as an athletic activity performance index of the subject if the tension state information is smaller than $\alpha_1$, an athletic activity performance index indicating that good performance can be achieved if the tension state information is greater than $\alpha_1$ and smaller than $\alpha_2$, and an athletic activity performance index indicating that the tension is too much to achieve good performance if the tension state information is greater than $\alpha_2$. When there is a monotonically decreasing relationship between the tension state information and the tension level with $\beta_1$ and $\beta_2$ being thresholds satisfying $\beta_1 < \beta_2$, the athletic activity performance index estimator 330 estimates an athletic activity performance index indicating that the tension is too much to achieve good performance as an athletic activity performance index of the subject if the tension state information is smaller than $\beta_1$, an athletic activity performance index indicating that good performance can be achieved if the tension state information is greater than $\beta_1$ and smaller than $\beta_2$, and an athletic activity performance index indicating that the tension is insufficient to achieve good performance if the tension state information is greater than $\beta_2$.

According to the invention of the present embodiment, it is possible to estimate the performance of an athletic activity that a subject is going to perform on the basis of the subject's state before starting the athletic activity.

<Supplementary Description>

As a single hardware entity, each device according to the present invention includes, for example, an input unit to which a keyboard or the like is connectable, an output unit to which a liquid crystal display or the like is connectable, a communication unit to which a communication apparatus (for example, a communication cable) that allows communication with the outside of the hardware entity is connectable, a CPU (Central Processing Unit, which may include a cache memory, a register, and the like), memories such as a RAM and a ROM, an external storage device such as a hard disk, and a bus that connects the input unit, the output unit, the communication unit, the CPU, the RAM, the ROM, and the external storage device such that data can be exchanged between them. If necessary, the hardware entity may be provided with a device (drive) that can read and write data from and to a recording medium such as a CD-ROM or the like. A physical entity provided with such hardware resources includes a general purpose computer or the like.

The external storage device of the hardware entity stores a program required to implement the functions described above and data or the like required in the processing of the program (not only the external storage device but also, for example, a ROM which is a read only storage device may store the program). Data or the like obtained through the processing of the program is stored in the RAM or the external storage device as appropriate.

In the hardware entity, the program stored in the external storage device (or the ROM or the like) and data required for the processing of the program are read into a memory as needed and are interpreted, executed, or processed by the CPU as appropriate. As a result, the CPU implements the predetermined functions (the components referred to above as "... ors", "... ers", "... units", "... means", or the like).

The present invention is not limited to the embodiments described above and appropriate modifications can be made without departing from the spirit of the present invention. The steps of processing described in the above embodiments may be executed not only in chronological order as described but also in parallel or individually as necessary or depending on the processing capabilities of the apparatuses that execute the steps of processing.

When the processing functions of the hardware entity (the device of the present invention) described in the above embodiments are implemented by a computer, the processing details of the functions that the hardware entity may have are described in a program. When the program is executed by a computer, the processing functions of the hardware entity are implemented on the computer.

The program in which the processing details are described can be recorded on a computer-readable recording medium. The computer-readable recording medium can be any type of medium such as a magnetic recording device, an optical disc, a magneto-optical recording medium, or a semiconductor memory. For example, a hard disk device, a flexible disk, a magnetic tape, or the like can be used as the magnetic recording device, a DVD (Digital Versatile Disc), a DVD-RAM (Random Access Memory), a CD-ROM (Compact Disc Read Only Memory), a CD-R (Recordable)/RW (Re-Writable), or the like can be used as the optical disc, an MO (Magneto-Optical disc) or the like can be used as the magneto-optical recording medium, and an EEP-ROM (Electronically Erasable and Programmable Read-Only Memory) or the like can be used as the semiconductor memory.

The program is distributed, for example, by selling, giving, or lending a portable recording medium such as a DVD or a CD-ROM with the program recorded on it. The program may also be distributed by storing the program in a storage device of a server computer and transmitting the program from the server computer to another computer through a network.

For example, a computer configured to execute such a program first stores, in its storage device, the program recorded on the portable recording medium or the program transmitted from the server computer. Then, the computer reads the program stored in its storage device and executes processing in accordance with the read program. In a different mode of execution of the program, the computer may read the program directly from the portable recording medium and execute processing in accordance with the read program and may also sequentially execute processing in accordance with the program transmitted from the server computer each time the program is received from the server computer. In another configuration, the processing may be executed through a so-called ASP (Application Service Provider) service in which functions of the processing are implemented just by issuing an instruction to execute the program and obtaining results without transmission of the program from the server computer to the computer. The program of this mode includes information that is provided for use in processing by a computer and is equivalent to the program (such as data having properties defining the processing executed by the computer rather than direct commands to the computer).

In this mode, the hardware entity is described as being configured by executing the predetermined program on the computer, but at least a part of the processing may be implemented in hardware.

The invention claimed is:

1. An athletic activity performance estimation device for estimating an athletic activity performance index relating to an athletic activity in which a subject performs a short-time action after a predetermined waiting time using information correlated with a state of tension of the subject as tension state information, an index indicating a tension level of the subject as a tension state index, and an index indicating a quality of performance of an athletic activity of the subject as the athletic activity performance index, the athletic activity performance estimation device comprising:
a memory configured to store computer-readable instructions; and
a processor coupled to the memory, the processor, upon executing the computer-readable instructions, is configured to:
acquire the tension state information of the subject before starting the athletic activity,
calculate the tension state index of the subject from the tension state information,
estimate the athletic activity performance index of the subject from the tension state index on the basis of a pre-given correlation curve between the tension state index and the athletic activity performance index, and
visually output the athletic activity performance index,
wherein the correlation is such that the athletic activity performance index monotonically increases with respect to the tension state index in a range in which the tension state index is smaller than a predetermined threshold and monotonically decreases with respect to the tension state index in a range in which the tension state index is greater than the threshold.

2. The athletic activity performance estimation device according to claim 1, wherein the processor is configured to, when $\theta_1$ and $\theta_2$ are thresholds satisfying $\theta_1 < \theta_2$, estimate an athletic activity performance index indicating that tension is insufficient to achieve good performance as an athletic activity performance index of the subject if the tension state index is smaller than $\theta_1$, an athletic activity performance index indicating that good performance can be achieved if the tension state index is greater than $\theta_1$ and smaller than $\theta_2$, and an athletic activity performance index indicating that tension is too much to achieve good performance if the tension state index is greater than $\theta_2$.

3. The athletic activity performance estimation device according to claim 1, wherein the athletic activity includes one of a long jump, a high jump, a ski/snow board jump, a high dive, and a soccer penalty kick.

4. The athletic activity performance estimation device according to claim 1, wherein the tension state information includes at least one of heartbeat, pulse wave, sweating, eye movement, body movement, and voice of the subject.

5. The athletic activity performance estimation device according to claim 4, wherein the tension state information is measured prior to the subject performing the athletic activity.

6. The athletic activity performance estimation device according to claim 5, wherein the tension state index includes predetermined frequency components of a heartbeat variability analysis on the heartbeat of the subject.

7. The athletic activity performance estimation device according to claim 1, wherein the athletic activity performance index is visually outputted as a graph.

8. The athletic activity performance estimation device according to claim 1, wherein the subject controls the state of tension of the subject, based on the athletic activity performance index that is visually outputted, to enter a state of tension that increases an athletic performance of the subject when performing the athletic activity.

9. An athletic activity performance estimation device for estimating an athletic activity performance index relating to an athletic activity in which a subject performs a short-time action after a predetermined waiting time using information correlated with a state of tension of the subject as tension state information, and an index indicating a quality of performance of an athletic activity of the subject as the athletic activity performance index, the athletic activity performance estimation device comprising:

a memory configured to store computer-readable instructions; and a processor coupled to the memory, the processor, upon executing the computer-readable instructions, is configured to:

acquire the tension state information of the subject before starting the athletic activity, estimate the athletic activity performance index of the subject from the tension state information on the basis of a pre-given correlation curve between the tension state information and the athletic activity performance index, and visually output the athletic activity performance index, wherein the correlation is such that the athletic activity performance index monotonically increases with respect to the tension state index in a range in which the tension state index is smaller than a predetermined threshold and monotonically decreases with respect to the tension state index in a range in which the tension state index is greater than the threshold.

10. The athletic activity performance estimation device according to claim 9, wherein the athletic activity performance index estimator is configured to, when there is a monotonically increasing relationship between the tension state information and the tension level with $\alpha_1$ and $\alpha_2$ being thresholds satisfying $\alpha_1 < \alpha_2$, estimate an athletic activity performance index indicating that tension is insufficient to achieve good performance as an athletic activity performance index of the subject if the tension state information is smaller than $\alpha_1$, an athletic activity performance index indicating that good performance can be achieved if the tension state information is greater than $\alpha_1$ and smaller than $\alpha_2$, and an athletic activity performance index indicating that tension is too much to achieve good performance if the tension state information is greater than $\alpha_2$, and when there is a monotonically decreasing relationship between the tension state information and the tension level with $\beta_1$ and $\beta_2$ being thresholds satisfying $\beta_1 < \beta_2$, estimate an athletic activity performance index indicating that tension is too much to achieve good performance as an athletic activity performance index of the subject if the tension state information is smaller than $\beta_1$, an athletic activity performance index indicating that good performance can be achieved if the tension state information is greater than $\beta_1$ and smaller than $\beta_2$, and an athletic activity performance index indicating that tension is insufficient to achieve good performance if the tension state information is greater than $\beta_2$.

11. An athletic activity performance estimation method in which an athletic activity performance estimation device estimates an athletic activity performance index relating to an athletic activity in which a subject performs a short-time action after a predetermined waiting time using information correlated with a state of tension of the subject as tension state information, an index indicating a tension level of the subject as a tension state index, and an index indicating a quality of performance of an athletic activity of the subject as the athletic activity performance index, the athletic activity performance estimation method comprising:

acquiring the tension state information of the subject before starting the athletic activity;

calculating the tension state index of the subject from the tension state information;

estimating the athletic activity performance index of the subject from the tension state index on the basis of a pre-given correlation curve between the tension state index and the athletic activity performance index; and visually outputting the athletic activity performance index, wherein the correlation is such that the athletic activity performance index monotonically increases with respect to the tension state index in a range in which the tension state index is smaller than a predetermined threshold and monotonically decreases with respect to the tension state index in a range in which the tension state index is greater than the threshold.

12. A non-transitory computer-readable medium storing a program for causing a computer to perform the athletic activity performance estimation method of claim 11.

* * * * *